(12) United States Patent
Gaudin et al.

(10) Patent No.: US 7,494,968 B2
(45) Date of Patent: Feb. 24, 2009

(54) NON-CYCLIC HINDERED KETONES AS PERFUMING INGREDIENT

(75) Inventors: Jean-Marc Gaudin, Annemasse (FR); Pascal Millet, Chambesy (CH)

(73) Assignee: Firmenich SA, Geneva (CH)

( * ) Notice: Subject to any disclaimer, the term of this patent is extended or adjusted under 35 U.S.C. 154(b) by 212 days.

(21) Appl. No.: 11/528,973

(22) Filed: Sep. 27, 2006

(65) Prior Publication Data
US 2007/0021320 A1    Jan. 25, 2007

Related U.S. Application Data

(63) Continuation of application No. PCT/IB2005/001265, filed on May 2, 2005.

(30) Foreign Application Priority Data
May 13, 2004    (WO) ................ PCT/IB2004/001607

(51) Int. Cl.
*D06L 3/30*    (2006.01)
(52) U.S. Cl. .............. 512/24; 8/107; 8/108; 8/111; 8/186; 252/186.1; 252/186.3; 252/186.26; 252/186.27
(58) Field of Classification Search .......... 512/24; 252/186
See application file for complete search history.

(56) References Cited

U.S. PATENT DOCUMENTS

| 4,544,714 A | 10/1985 | Ochsner | 252/522 |
| 4,654,169 A * | 3/1987 | Ochsner | 512/20 |
| 6,252,120 B1 | 6/2001 | Dilk et al. | 568/393 |
| 6,645,254 B1 * | 11/2003 | Aida et al. | 8/107 |
| 6,720,295 B2 * | 4/2004 | Vanhessche et al. | 510/101 |

FOREIGN PATENT DOCUMENTS

| EP | 0 085 352 B1 | 1/1986 |
| EP | 1 138 755 A2 | 10/2001 |
| JP | 63203609 | 8/1988 |

OTHER PUBLICATIONS

English Abstract: JP 2001 271087 XP002338106—"Chemically stable perfumes containing 2,4-dimethyl-3-pentanones and bleaching agents containing them" (2001).

* cited by examiner

*Primary Examiner*—Mark Eashoo
*Assistant Examiner*—Mohammad R Asdjodi
(74) *Attorney, Agent, or Firm*—Winston & Strawn LLP

(57) ABSTRACT

The present invention relates to the use as perfuming ingredient of a compound of formula

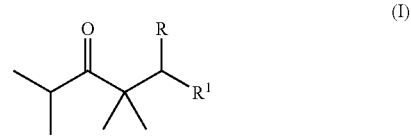

(I)

wherein R represents a hydrogen atom or a methyl or ethyl group, and
$R^1$ represents (i) a $(Me)(R^2)C=C(R^3)$ group, $R^2$ representing a hydrogen atom or a methyl group and $R^3$ representing a methyl or ethyl group, or (ii) a phenyl group optionally substituted by one or two methyl groups;
as well as to the compositions or articles associated with these compounds.

12 Claims, No Drawings

NON-CYCLIC HINDERED KETONES AS PERFUMING INGREDIENT

CROSS-REFERENCE TO RELATED APPLICATIONS

This application is a continuation of International application PCT/IB2005/001265 filed May 2, 2005, the entire content of which is expressly incorporated herein by reference thereto.

TECHNICAL FIELD

The present invention relates to the field of perfumery. More particularly, it concerns the use as perfuming ingredient of a compound of formula

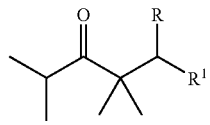

wherein R represents a hydrogen atom or lower alkyl group, and $R^1$ represents a $(Me)(R^2)C=C(R^3)$ group or a phenyl group optionally substituted.

BACKGROUND

Compounds having fragrances of the citrus type, and in particular of the grapefruit odor, are of high interest for the perfumery industry as they can be used in a variety of articles to impart a very well appreciated scent.

Most of the compounds of formula (I) wherein $R^1$ represents a phenyl group are known from the prior art. Indeed U.S. Pat. No. 4,654,169 cites several of them as intermediates in the synthesis of oximes. However, this prior art document does not report or suggest any organoleptic properties of the compounds of formula (I), or any use of said compound in the field of perfumery.

The compounds of formula (I) wherein $R^1$ represents a substituted carbon-carbon double bond have never been reported in the prior art. The closest known analogue of said compounds is 2,4,4,7-tetramethyloct-6-en-3-one which has been described in U.S. Pat. No. 6,252,120 as perfuming ingredient. However, this prior art document does not report or suggest any compound of the present invention and still less their organoleptic properties or any use of said compound in the field of perfumery.

SUMMARY OF THE INVENTION

The present invention relates to the use as perfuming ingredients of a compound of formula (I), as defined below. Another aspect of the invention concerns novel compounds of formula (II), which represents a particular embodiment of the invention. Further aspects of the invention are the perfuming compositions and the perfumed articles associated with said compounds.

DETAILED DESCRIPTION OF THE PREFERRED EMBODIMENTS

We have now discovered that a compound of formula

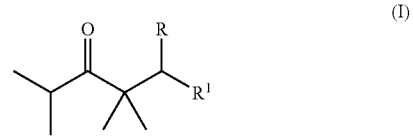

wherein R represents a hydrogen atom or a methyl or ethyl group, and $R^1$ represents
(i) a $(Me)(R^2)C=C(R^3)$ group, $R^2$ representing a hydrogen atom or a methyl group and $R^3$ representing a methyl or ethyl group; or
(ii) a phenyl group optionally substituted by one or two methyl groups; is a useful perfuming ingredient, which is unexpectedly characterized by a citrus odor of the grapefruit type.

According to a preferred embodiment, the preferred compounds of formula (I) are those wherein R represents a hydrogen atom, in particular those wherein $R^1$ represents (i) a $(Me)_2C=C(R^3)$ group, $R^3$ representing a methyl or ethyl group, or (ii) a phenyl group optionally substituted by one methyl group.

The invention's compounds of formula

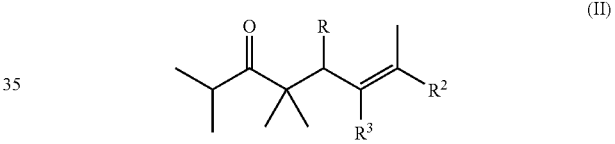

wherein the carbon-carbon double bond has a configuration of the type (Z) or (E), or a mixture of the two configurations, and R, $R^2$ and $R^3$ have the meaning indicated for formula (I), are new and are also an object of the present invention. Amongst the compounds (II), the one wherein R is a hydrogen atom and $R^2$ and $R^3$ are each a methyl group is a preferred embodiment of the invention.

As mentioned above, all the invention's compounds are characterized by a citrus type odor, of the grapefruit type.

In particular one can cite 2,2,4-trimethyl-1-phenyl-3-pentanone which has a pleasant, sparkling and natural grapefruit fragrance wherein are also present balsamic and floral notes as well as bottom notes of the ginger and herbal-green type. The overall impression is a bit bitter and reminiscent of the grapefruit peel. The fragrance is also characterized by a good persistence and is also one of the most powerful grapefruit notes ever observed for a non-sulfur containing compound.

Other examples of invention's compounds are 2,2,4-trimethyl-1-(2-methylphenyl)-3-pentanone or 2,4,4-trimethyl-5-phenyl-3-hexanone which have a grapefruit, slightly sulfury, odor.

Yet, another invention's compound is the 2,4,4,6,7-pentamethyl-6-octen-3-one that has a fresh and sparkling grapefruit fragrance wherein are also present linalool, fresh-mint citrata, cooling-fresh and cinnamon tonalities. Another important characteristic of said compound is its woody-aromatic aspect. Bottom notes of the floral, clary-sage are also present. The overall impression of the 2,4,4,6,7-pentamethyl- 6-octen-3-one fragrance reminds of the grapefruit peel, but without the sulfury aspect, and the floral-herbaceous aspect of the clary-sage.

The fragrance of 2,4,4,6,7-pentamethyl-6-octen-3-one is also distinct from the one of the prior art compound 2,4,4,7-tetramethyl-6-octen-3-one. Indeed, the invention's compound has an odor which is characteristic of the grapefruit peel with a woody (pine)-aromatic note, while the prior art compound has an odor which is characteristic of the grapefruit juice, bergamot, and is not woody.

As mentioned above, the invention concerns also the use of a compound of formula (I) as perfuming ingredients. Said compound of formula (I) can be used as such or in admixture with one or more other compounds of formula (I). In other words another object of the present invention concerns a method to confer, enhance, improve or modify the odor properties of a perfuming composition or of a perfumed article, which method comprises adding to said composition or article an effective amount of at least a compound of formula (I).

By "use of a compound of formula (I)" it has to be understood here also the use of any composition containing the compound (I).

Said compositions, which are in fact perfuming compositions that can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. As solid carrier one may cite, as non-limiting examples, absorbing gums or polymers, or yet encapsulating materials. Examples of such materials may comprise, for example, wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparations or compositions to impart an hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier than those previously specified can also be ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I); and ii) a consumer product base, is also an object of the present invention.

For the sake of clarity, it has to be mentioned that, by "consumer product base", we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The use of, or a composition or article containing, 2,2,4-trimethyl-1-phenyl-3-pentanone and/or 2,4,4,6,7-pentamethyl-6-octen-3-one is a particularly appreciated embodiment of the present invention.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.5% to 35% by weight, or even more, of the compounds of the invention based on the weight of the composition into which they are incorporated. Concentrations lower than these, such as in the order of 1% to 15% by weight, can be used when these compounds are incorporated into perfumed articles.

The invention's compounds can be prepared by a process comprising the reaction of the 2,4-dimethyl-pentan-3-one with the appropriate alkylating agent such a benzyl halide or an allyl halide, in the presence of a base, according to the Scheme (I).

Scheme (I):
Specific examples of preparation of the compounds of formula (I)

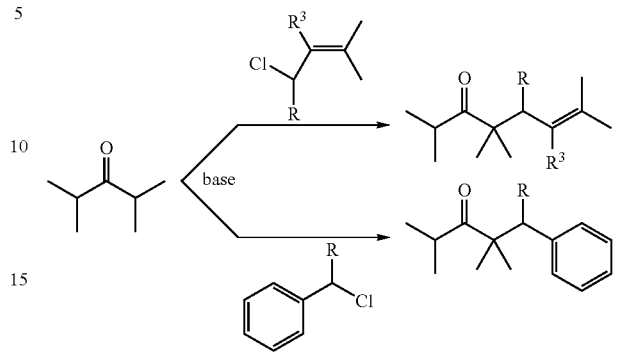

wherein R and $R^3$ have the same meaning as indicated above. Specific examples of preparation are given in the Examples.

EXAMPLES

The following examples are illustrative of the present invention's embodiments, and further demonstrate the advantages of the invention relative to the prior art teachings.

The abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Synthesis of 2,4,4,6,7-pentamethyl-6-octen-3-one

On a three neck flask containing 50 ml of dry THF, at −70° C., were added 65 ml of a 1.5 M solution of LDA THF in cyclohexane (96 mmoles). To said solution were added, dropwise, 10 g of 2,4-dimethyl-3-pentanone (87.5 mmoles). After one hour stirring, the medium temperature was left to warm up to 0° C., and then 14.3 g of 2,3-dimethyl-1-bromo-2-butene (87 mmoles) were added dropwise so as to maintain the reaction temperature between 0° and 10° C. At the end of the addition of the bromide, the temperature was risen to room temperature. After one hour stirring the reaction medium was poured into an excess of a 2 M aqueous HCl solution. The mixture thus obtained was extracted with 100 ml of cyclohexane and the organic layer washed with water until neutrality.

Drying of the organic layer, evaporation of the solvent and distillation (B.p.$_{-4.5\ mbar}$=84° C.) of the crude oil afforded the title compound with a yield of 72%.

$^{13}C$-NMR: 20.3(q); 20.9(q); 21.0(q); 21.5(q); 24.3(q); 34.4 (d); 42.3(t); 49.5(s); 124.5(s); 128.3(s); 220.3(s).

$^1H$-NMR: 1.05(d, J=6 Hz, 6H); 1.13(s, 6H); 1.61(s, 3H); 1.66(s, 6H); 2.34(s, 2H); 3.16(m, 1H).

Example 2

Synthesis of Compounds of Formula (I) Having a Phenyl Group a) Synthesis of 2,2,4-trimethyl-1-phenyl-3-pentanone To a 2 M solution of lithium diisopropylamide (LDA) in THF/n-heptane (175 mmoles) were added, at 0° C., 20 g of diisopropyl ketone (175 mmoles). After 1 hour stirring at 0° C., were added to the reaction medium 22.2 g of benzyl chloride (175 mmoles) and the reaction temperature was allowed to rise up to room temperature. After stirring overnight at 50° C., the reaction was stopped by the addition of an excess of a 2 M HCl aqueous solution. Then, the reaction medium was extracted with $Et_2O$, the organic layer was dried ($Na_2SO_4$) and the solvent evaporated.

Distillation of the crude product provided (B.p.$_{0.6\ mbar}$=55-60° C.) the title compound (yield=72%)

$^{13}$C-NMR: 19.9(q); 23.9(q); 34.6(d); 44.5(t); 48.9(s); 126.3(d); 127.9(d); 130.6(d); 137.9(s); 219.6(s).

$^1$H-NMR: 1.0(d, J=6 Hz, 6H); 1.12(s, 6H); 1.81(s, 2H); 3.07(m, 1H); 7.10(m, 2H); 7.23(m, 3H).

b) Synthesis of 2,2,4-trimethyl-1-(2-methylphenyl)-3-pentanone

The title compound was obtained by using the same experimental procedure as described under a), but using 2-methylbenzyl chloride as alkylating agent.

Distillation of the crude product provided (B.p.$_{0.7\ mbar}$=75° C.) the title compound (yield=40%)

$^{13}$C-NMR: 20.1(q); 20.5(q); 23.7(q); 34.6(d); 39.7(t); 49.6 (s); 125.4(d); 126.3(d); 130.5(d); 131.1(d); 136.3(s); 137.1 (s); 220.0(s).

$^1$H-NMR: 1.05(d, J=6 Hz, 6H); 1.15(s, 6H); 2.31(s, 3H); 2.87(s, 2H); 3.12(m, 1H); 7.10(m, 4H).

c) Synthesis of 2,4,4-trimethyl-5-phenyl-3-hexanone

The title compound was obtained by using the same experimental procedure as described under a), but using 1-chloro-1-phenylethane as alkylating agent.

Distillation of the crude product provided (B.p.$_{0.75\ mbar}$=80° C.) the title compound (yield=61%)

$^{13}$C-NMR: 16.4(q); 19.0(q); 20.0(q); 20.3(q); 24.1(q); 34.7 (d); 44.9(d); 51.8(s); 126.5(d); 127.8(d); 129.4(d); 142.5(s); 220.1(s).

$^1$H-NMR: 0.98(s, 3H); 1.0(d, J=6 Hz, 3H); 1.03(d, J=6 Hz, 3H); 1.09(s, 3H); 1.16(d, J=6 Hz, 3H); 3.10(m, 1H); 3.23(q, J=6 Hz, 1H); 7.20(m, 3H); 7.27(m, 2H).

Example 3

Preparation of a Perfuming Composition

An eau de toilette of the citrus-floral type was prepared by admixing the following ingredients:

| Ingredient | Parts by weight |
| --- | --- |
| Benzyl acetate | 20 |
| 10%* Cis-3-Hexenol acetate | 40 |
| 10%* Acetophenone | 45 |
| 10%* Aldehyde C10 | 50 |
| 10%* Aldehyde C12 | 30 |
| 10%* Aldehyde C8 | 100 |
| 10%* Aldehyde C9 | 10 |
| 10%* Ethyl butyrate | 15 |
| Allyl caproate | 20 |
| 10%* (−)-(R)-1(6),8-p-Menthadien-2-one | 15 |
| 10%* Cis-3-Hexenol | 30 |
| Citral | 5 |
| 4-cyclohexyl-2-methyl-2-butanol [1] | 80 |
| 10%* Allyl cyclohexylpropionate | 5 |
| 10%* Damascone beta [1] | 20 |
| 10%* γ-n-decalactone | 80 |

-continued

| Ingredient | Parts by weight |
| --- | --- |
| 4-(2,6,6-Trimethyl-1-cyclohexen-1-yl)-2-butanone | 20 |
| Geraniol | 10 |
| HEDIONE ® [2] | 100 |
| Ionone Beta | 25 |
| Phenylethyl isobutyrate | 10 |
| Lime | 120 |
| Limonene | 1100 |
| Linalool | 400 |
| Mandarine essential oil | 80 |
| 4-Nonanolide | 10 |
| Phenoxyethanol | 55 |
| 0.01%* (1R,4R)-8-Mercapto-3-p-menthanone | 40 |
| Terpineol | 30 |
| 2,4-Dimethyl-3-cyclohexen-1-carboxaldehyde[3] | 25 |
| 10%* Vert de Fleur d'oranger 115 SA[3] | 10 |
| | 2600 |

* in dipropyleneglycol
[1] origin: Firmenich SA, Geneva, Switzerland
[2] Methyl dihydrojasmonate; origin: Firmenich SA, Geneva, Switzerland
[3] origin: International Flavors & Fragrances, USA
[4] Compounded perfumery base, origin: Firmenich SA, Geneva, Switzerland The addition of 1000 parts by weight of 2,4,4,6,7-pentamethyl-6-octen-3-one to the above-described composition imparted to the latter a new dimension. The new eau de toilette thus obtained had a more enhanced floral-citrus character and its fragrance was also more sparkling, almost effervescent, with also a note that was both pink grapefruit and floral, slightly freesia.

On the other hand, the addition of the same amount of 2,2,4-trimethyl-1-phenyl-3-pentanone imparted to the above-mentioned eau de toilette a tonality which was more citrus, bitter and rhubarb as well as less floral.

Example 4

Preparation of a Perfuming Composition

An eau de toilette of the citrus-fruity type was prepared by admixing the following ingredients:

| Ingredient | Parts by weight |
| --- | --- |
| Benzyl acetate | 250 |
| Cis-3-Hexenol acetate | 25 |
| Styrallyl acetate | 35 |
| Hexylcinnamic aldehyde | 200 |
| Artemisia | 50 |
| Methyl benzoate | 15 |
| Camphor | 40 |
| (−)-(R)-1(6),8-p-Menthadien-2-one | 25 |
| 3,7-Dimethyl-6-octenenitrile | 15 |
| 2,6-Dimethyl-7-octen-2-ol | 400 |
| 1-Allyl-4-methoxybenzene | 25 |
| Eucalyptus Globulus | 40 |
| Eugenol | 40 |
| HEDIONE ® [1] | 100 |
| Allyl heptanoate | 20 |
| 2-Phenoxyethyl isobutyrate | 100 |
| LILIAL ® [2] | 130 |
| 10%* Methyl Octyne carbonate | 10 |
| Methylparacresol | 10 |
| p-tert-Butylcyclohexyl acetate | 200 |
| ROMANDOLIDE ® [3] | 100 |
| SCLAREOLATE ® [4] | 50 |

-continued

| Ingredient | Parts by weight |
|---|---|
| Terpineol | 80 |
| 2,4-Dimethyl-3-cyclohexen-1-carboxaldehyde [3)] | 40 |
| | 2000 |

* in dipropyleneglycol
[1)] Methyl dihydrojasmonate; origin: Firmenich SA, Geneva, Switzerland
[2)] 3-(4-Tert-butylphenyl)-2-methylpropanal; origin: Givaudan-Roure SA, Vernier, Suisse
[3)] (1S,1'R)-[1-(3',3'-Dimethyl-1'-cyclohexyl)ethoxycarbonyl]methyl propanoate; origin: Firmenich SA, Geneva, Switzerland
[4)] Propyl (S)-2-(1,1-dimethylpropoxy)propanoate; origin: Firmenich SA, Geneva, Switzerland The addition of 400 parts by weight of 2,4,4,6,7-pentamethyl-6-octen-3-one to the above-described composition imparted to the latter a very interesting pink grapefruit twist with a pine-woody side. Furthermore, the fragrance of the new eau de toilette acquired a more sparkling character, with a citrus-fruity tonality much more natural.

The addition of the same amount of 2,2,4-trimethyl-1-phenyl-3-pentanone to the eau de toilette imparted to the latter a similar olfactive effect to the one obtained by the addition of 2,4,4,6,7-pentamethyl-6-octen-3-one, however the effect was more persistent.

On the other hand, the addition of 400 parts by weight of 2,4,4,7-tetramethyl-6-octen-3-one (of the prior art) to the above-described composition imparted to said composition a fragrance of the terpenic, acid type, close to the limette type. This fragrance, which contains the prior art compound, was also devoid of the pink grapefruit character, as well as of the woody aspect, obtained with the addition of the invention's compounds.

What is claimed is:

1. A compound of formula

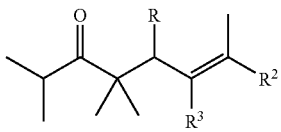

(II)

wherein the carbon-carbon double bond has a configuration of the type (Z) or (E), or a mixture of the two configurations;
R represents a hydrogen atom or a methyl or ethyl group, and
$R^2$ represents a hydrogen atom or a methyl group and $R^3$ represents a methyl or ethyl group.

2. A compound according to claim 1, wherein said compound is 2,4,4,6,7-pentamethyl-6-octen-3-one.

3. A perfuming composition comprising
i) as perfuming ingredient, at least one compound of formula

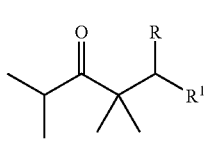

(I)

wherein R represents a hydrogen atom or a methyl or ethyl group, and $R^1$ represents a $(Me)(R^2)C=C(R^3)$ group, $R^2$ representing a hydrogen atom or a methyl group and $R^3$ representing a methyl or ethyl group;
ii) at least one ingredient selected from the group consisting of a perfumery carrier and a perfumery base; and
iii) optionally at least one perfumery adjuvant.

4. A perfuming composition according to claim 3, wherein the compound of formula (I) is one wherein R represents a hydrogen atom and $R^1$ represents a $(Me)_2C=C(R^3)$ group, $R^3$ representing a methyl or ethyl group.

5. A perfuming composition according to claim 3, wherein the compound of formula (I) is 2,4,4,6,7-pentamethyl-6-octen-3-one.

6. A perfumed article comprising:
i) as perfuming ingredient, at least one compound of formula

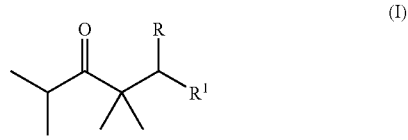

(I)

wherein R represents a hydrogen atom or a methyl or ethyl group, and $R^1$ represents a $(Me)(R^2)C=C(R^3)$ group, $R^2$ representing a hydrogen atom or a methyl group and $R^3$ representing a methyl or ethyl group; and
ii) a consumer product base.

7. A perfumed article according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

8. A method to confer, enhance, improve or modify the odor properties of a perfuming composition or of a perfumed article, which method comprises adding to said composition or article an effective amount of at least a compound of formula

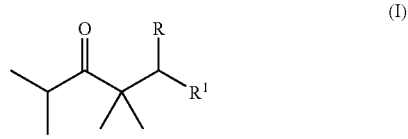

(I)

wherein R represents a hydrogen atom or a methyl or ethyl group, and $R^1$ represents a $(Me)(R^2)C=C(R^3)$ group, $R^2$ representing a hydrogen atom or a methyl group and $R^3$ representing a methyl or ethyl group.

9. A perfuming composition comprising:
i) as perfuming ingredient, at least one compound according to claim 1;
ii) at least one ingredient selected from the group consisting of a perfumery carrier and a perfumery base; and
iii) optionally at least one perfumery adjuvant.

10. A perfumed article comprising:
i) as perfuming ingredient, at least one compound according to claim 1; and
ii) a consumer product base.

11. A perfumed article according to claim 10, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

12. A method to confer, enhance, improve or modify the odor properties of a perfuming composition or of a perfumed article, which method comprises adding to said composition or article an effective amount of at least a compound according to claim 1.

* * * * *